United States Patent
Yoo et al.

(10) Patent No.: US 11,934,555 B2
(45) Date of Patent: Mar. 19, 2024

(54) PRIVACY-PRESERVING DATA CURATION FOR FEDERATED LEARNING

(71) Applicant: SIEMENS HEALTHINEERS AG, Forchheim (DE)

(72) Inventors: Youngjin Yoo, Princeton, NJ (US); Gianluca Paladini, Skillman, NJ (US); Eli Gibson, Plainsboro, NJ (US); Pragneshkumar Patel, East Windsor, NJ (US); Poikavila Ullaskrishnan, Lebanon, NH (US)

(73) Assignee: Siemens Healthineers AG, Forchheim (DE)

( * ) Notice: Subject to any disclaimer, the term of this patent is extended or adjusted under 35 U.S.C. 154(b) by 197 days.

(21) Appl. No.: 17/449,190

(22) Filed: Sep. 28, 2021

(65) Prior Publication Data
US 2023/0102732 A1    Mar. 30, 2023

(51) Int. Cl.
| | | |
|---|---|---|
| *G06F 21/62* | (2013.01) | |
| *G06N 20/00* | (2019.01) | |
| *G06N 20/20* | (2019.01) | |
| *G16H 30/40* | (2018.01) | |
| *G16H 50/20* | (2018.01) | |
| *G16H 50/70* | (2018.01) | |
| *G16H 80/00* | (2018.01) | |

(52) U.S. Cl.
CPC ...... *G06F 21/6245* (2013.01); *G06F 21/6254* (2013.01); *G06N 20/20* (2019.01); *G16H 50/20* (2018.01); *G16H 50/70* (2018.01); G06N 20/00 (2019.01); G16H 30/40 (2018.01); G16H 80/00 (2018.01)

(58) Field of Classification Search
CPC .. G06F 21/62; G06F 21/6218; G06F 21/6245; G06F 21/6254; G16H 30/40; G16H 50/20; G16H 50/70; G16H 80/00; G06N 20/00; G06N 20/20
See application file for complete search history.

(56) References Cited

U.S. PATENT DOCUMENTS

| | | | |
|---|---|---|---|
| 2011/0110568 A1* | 5/2011 | Vesper | G06Q 10/10 382/128 |
| 2020/0293887 A1 | 9/2020 | De Brouwer et al. | |

(Continued)

OTHER PUBLICATIONS

A. Vaid, et al., "Federated learning of electronic health records to improve mortality prediction in hospitalized patients with covid-19: Machine learning approach," International Journal for Quality in Health Care, vol. 9, Jan. 2021.

(Continued)

*Primary Examiner* — D'Arcy Winston Straub

(57) ABSTRACT

Systems and methods facilitate privacy-preserving data curation in a federated learning system by transmitting a portion of a potential data sample to a remote location. The portion is inspected for quality to rule out data samples that do not satisfy data curation criteria. The remote examination focuses on checking the region of interest but maintains privacy as the examination is unable to parse any other identifiable subject information such as face, body shape etc. because pixels or voxels outside the portion are not included. The examination results are sent back to the collaborators so that inappropriate data samples can be excluded during federated learning rounds.

20 Claims, 4 Drawing Sheets

(56) References Cited

U.S. PATENT DOCUMENTS

2021/0035015 A1* 2/2021 Edgar ............... G06F 18/211
2021/0150269 A1* 5/2021 Choudhury ........ G06V 30/1985
2022/0083904 A1* 3/2022 Pastore ............... G06N 3/04
2023/0031052 A1* 2/2023 McAfoose ........... G06N 20/20

OTHER PUBLICATIONS

F. Qian and A. Zhang, "The value of federated learning during and post-covid-19,"International Journal for Quality in Health Care, vol. 33, Feb. 2021.

Flores, Mona, et al. "Federated Learning used for predicting outcomes in SARS-COV-2 patients." Research Square (2021).

H. Brendan McMahan, E. Moore, D. Ramage, S. Hampson, and B. Ag uera y Arcas, "Communication-efficient learning of deep networks from decentralized data," ArXiv e-prints, pp. arXiv-1602, 2016.

L. Luo, Y. Xiong, Y. Liu, and X. Sun, "Adaptive gradient methods with dynamic bound of learning rate," arXiv preprint arXiv: 1902.09843, 2019.

L. Wang, S. Xu, X. Wang, and Q. Zhu, "Addressing class imbalance in federatedlearning," in Proceedings of the AAAI Conference on Artificial Intelligence, vol. 35,p. 10165-10173, 2021.

M. Duan, D. Liu, X. Chen, R. Liu, Y. Tan, and L. Liang, "Self-balancing federated learning with global imbalanced data in mobile systems," IEEE Transactions on Parallel and Distributed Systems, vol. 32, No. 1, pp. 59-71, 2020.

M. J. Sheller, B. Edwards, G. A. Reina, J. Martin, S. Pati, A. Kotrotsou, M. Milchenko, W. Xu, D. Marcus, R. R. Colen, et al., "Federated learning in medicine: facilitating multi-institutional collaborations without sharing patientdata," Scientific reports, vol. 10, No. 1, pp. 1-12, 2020.

M. Yang, A. Wong, H. Zhu, H. Wang, and H. Qian, "Federated learning with classimbalance reduction," arXiv preprint arXiv:2011.11266, 2020.

Q. Dou, et al. "Federated deep learning for detecting covid-19 lung abnormalities in ct: a privacy-preserving multinational validation study," npj Digit. Med., vol. 4, Mar. 2021.

Q. Yang, Y. Liu, T. Chen, and Y. Tong, "Federated machine learning: Concept and applications," ACM Transactions on Intelligent Systems and Technology (TIST), vol. 10, No. 2, pp. 1-19, 2019.

T. Li, A. K. Sahu, M. Zaheer, M. Sanjabi, A. Talwalkar, and V. Smith, "Federated optimization in heterogeneous networks," arXiv preprint arXiv:1812.06127, 2018.

Extended European Search Report (EESR) dated Feb. 23, 2023 in corresponding European Patent Application No. 22197917.2.

Rieke, Nicola et al.: "The Future of Digitial Health with Federated Learning", arxiv.org, Cornell University Library, 201 Olin Library Cornell University Ithaca, NY, 14853, Mar. 18, 2010.

* cited by examiner

PRIVACY-PRESERVING DATA CURATION FOR FEDERATED LEARNING

FIELD

The present embodiments relate to federated learning.

BACKGROUND

In the last few years deep learning has been elevated from an area of medical research into an area of medical products because of improvements in computing hardware and proliferation of healthcare data. Massive volumes of data are collected every day by large number of entities such as research centers, hospitals, or other medical entities. Analysis of the data could improve learning models and user experiences. The complex problem of training these models could be solved by distributed computing by taking advantage of the resource storage, computing power, cycles, content, and bandwidth of participating devices available at the edges of a network. In such a distributed machine learning scenario, the dataset is transmitted to or stored among multiple edge devices. The devices solve a distributed optimization problem to collectively learn the underlying model. For distributed computing, similar (or identical) datasets may be allocated to multiple devices that are then able to solve a problem in parallel. However, access to large, diverse healthcare datasets remains a challenge due to regulatory concerns over sharing protected healthcare information.

Privacy and connectivity concerns may prohibit data from being shared between entities preventing largescale distributed methods. Hospitals, for example, may prefer not to or may not be allowed to share medical data with other entities or unknown users. Federated learning is a distributed computing approach that enables entities to collaborate on machine learning projects without sharing sensitive data such as patient records, financial data, or classified secrets. The basic premise behind federated learning is that the model moves to meet the data rather than the data moving to meet the model. Therefore, the minimum data movement needed across the federation is the model parameters and their updates. Challenges still exist though in managing the flow of data, the training of models, and privacy issues.

SUMMARY

Systems, methods, and computer readable media are provided for data curation for a federated learning process.

In a first aspect, a method is provided for training a model using federated learning by a plurality of collaborators, the method comprising: receiving, by a collaborator of the plurality of collaborators, global model parameters from a parameter aggregation server; acquiring, by the collaborator, sample data; transmitting, by the collaborator, an anonymized portion of the sample data to a curation server configured to identify data samples that do or don't meet one or more data selection conditions; receiving, by the collaborator from the curation server, validation for the sample data; training, by the collaborator, the model using the validated sample data; and transmitting, by the collaborator, local model parameters for the model to the parameter aggregation server.

In a second aspect, a method is provided training a model using federated learning by a plurality of collaborators, the method comprising: receiving, by a collaborator of the plurality of collaborators, global model parameters from a parameter aggregation server; acquiring, by the collaborator, sample data; submitting, by the collaborator, an anonymized portion of the sample data to a machine trained model configured to identify data samples that don't meet data selection conditions; receiving, by the collaborator from the machine trained model, validation for the sample data; training, by the collaborator, the model using the validated sample data; and transmitting, by the collaborator, local model parameters for the model to the parameter aggregation server.

In a third aspect, a system for federated learning is provided. The system includes a plurality of collaborators, a curation server, and an aggregation server. Each collaborator of the plurality of collaborators is configured to acquire sample data, anonymize the sample data, and transmit the anonymized sample data to a curation server for validation. Each collaborator is further configured to train a local machine learned model using validated sample data, update local model weights for the local machine learned model, and send the updated local model weights to an aggregation server. The curation server is configured to receive the anonymized sample data and identify sample data that does or doesn't meet one or more data selection conditions. The aggregation server is configured to receive the updated model weights from the plurality of collaborators, calculate aggregated model weights, and transmit the aggregated model weights to the plurality of collaborators to update the local machine learned model.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Figure 1:
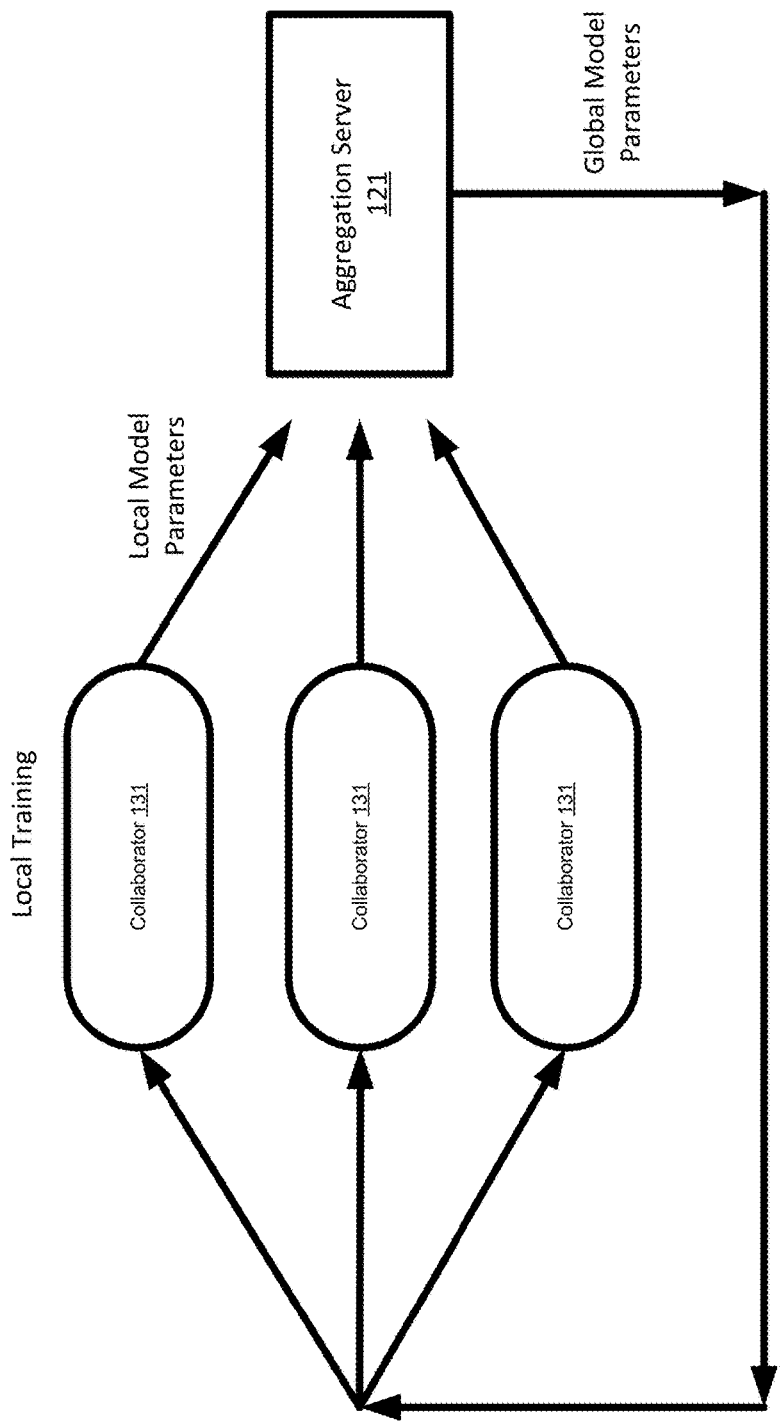
FIG. 1 depicts an example federated learning system.

Embodiments provide systems and methods for data curation for federated learning. Embodiments facilitate privacy-preserving data curation by transmitting a portion of a potential data sample to a remote location. The portion is inspected for quality to rule out data samples that do not satisfy data curation criteria. The remote examination focuses on visually checking the region of interest but maintains privacy as the examination is unable to parse any other identifiable subject information such as face, body shape etc. because voxels outside the portion are not included. The examination results are sent back to the collaborators so that inappropriate data samples can be excluded during federated learning rounds.

Federated learning (FL) is a distributed approach for training a model that includes multiple distributed devices/collaborators and at least one aggregation/central server. Each of the collaborators download a current model and computes an updated model at the collaborator itself (ala edge computing) using local data. The locally trained models are then sent from the collaborators back to the central server where the models or parameters are aggregated. A single consolidated and improved global model is sent back to the devices from the server. Different schemes and setups exist (for example peer to peer), but the basis of federated learning is that the local data stays at the local site and is not shared by collaborators. Federated learning allows for machine learning algorithms to gain experience from a broad range of data sets located at different locations. The approach enables multiple organizations to collaborate on the development of models, but without needing to directly share secure data with each other. Over the course of several training iterations, the shared models get exposed to a significantly wider range of data than what any single organization possesses in-house. In other words, federated learning decentralizes machine learning by removing the need to pool data into a single location. Instead, the model is trained in multiple iterations at different locations.

In an embodiment, the collaborators or remote locations include hospitals and medical centers. With federated learning, these sites can remain in full control and possession of their patient data with complete traceability of data access, limiting the risk of misuse by third parties. Existing medical data is typically not fully used by machine learning because the data resides in data silos or walled gardens and privacy concerns restrict access. Centralizing or releasing data, however, poses not only regulatory, ethical, and legal challenges, related to privacy and data protection, but also technical ones. Anonymizing, controlling access and safely transferring healthcare data is a non-trivial, and sometimes impossible task. Anonymized data from the electronic health record can appear innocuous and compliant with regulations, but just a few data elements may allow for patient reidentification. The same applies to genomic data and medical images making them as unique as a fingerprint. Therefore, unless the anonymization process destroys the fidelity of the data, likely rendering it useless, patient reidentification or information leakage cannot be ruled out. Hospitals and medical centers may thus make great use of federated learning.

FIG. 1 depicts an example of a federated learning system. As depicted, the federated learning system includes three collaborator devices/remote devices herein also referred to as collaborators 131 and a central/aggregation server 121. In a typical federated learning system, there may be tens, hundreds, thousands, or more devices/collaborators 131 depending on the application. Each collaborator 131 is configured to acquire local data for which to locally train a model over multiple rounds. To start the training, the aggregation server 121 sends global model parameters (for example model weights or a vector representing the weights) to all chosen collaborators 131 for initialization. Each collaborator 131 trains a local model (initialized with the global model parameters) with locally acquired data and updates the model parameters for certain epochs. The collaborators 131 then send updated model parameters back to the aggregation server 121. The aggregation server 121 aggregates the updated model parameters and then send the global model parameters to collaborators 131 for another round of training. The result is a system that allows the training data to remain securely onsite which increases both security and privacy. For certain models such as medical applications, data is now available to be used when previously privacy concerns and regulations may have prohibited its use. There are, however, potential drawbacks and complications that arise from the distributed nature of federated learning. In general, the minimum data movement needed across the federation is the model parameters and their updates.

Ensuring sufficiently large, curated datasets is needed to train modern AI models for achieving quality and generalizability in clinical practice. However, in the context of federated learning, the privacy-preservation purpose and decentralized nature of the clinical data complicate and hinder data curation procedure to ascertain clinical-grade accuracy, while being safe and generalizable to unseen data. Data curation is a crucial step in training deep networks on medical image data as non-relevant data samples can deteriorate training performance. Currently, data curation is typically conducted on centralized datasets or independently done in local collaborating institutions. For example, these selection tasks are typically done by manually examining an entire group of data samples that will be used. Data curation on centralized datasets does enable utilizing standardized selection criteria but could violate privacy preservation, which is a key benefit of federated learning. Data curation via remote desktop has been considered as an alternative solution but would still have a great risk to defeat patient privacy preservation because sensitive visual information can be still revealed. On the other hand, independent data curation in local collaborating institutions would not be able to utilize standardized procedure and would also lead to poor outcome due to inconsistency in curation procedures and involving examiners. It may be also not feasible due to required expert efforts at each site.

In federated learning, data curation may have greater impact on training deep networks than in centralized learning. Poor quality data samples could disturb more seriously for collaborators 131 having small data during federated learning rounds. Depending on the robustness of the federated learning model aggregation, this could have a significant impact on overall federated learning progress and may lead to instable federated learning rounds. Embodiments provide consistent data curation that can promote enhanced federated learning training stability and generalizability without violating privacy preservation, that are essential requirements for large scale clinical adoption. Data availability is an important hurdle for implementation of AI methods in clinical practice. By providing data curation procedure that does not violate the purpose of federated learning, embodiments help to increase high quality data availability.

Embodiments described herein provide for distributed processing of data while maintaining privacy and transmission concerns. The training of a model occurs in a decentralized manner with multiple collaborators 131 with only the local data available to each collaborator 131. The multiple collaborators 131 do not share data. In an embodiment, an aggregation of model parameters occurs on an aggregation server 121. While the rest of this documents describes an aggregation scheme, embodiments may be applicable to any federated learning scheme where sample data is not shared between sites. For example, the federated learning system may use a peer to peer sharing strategy where the collaborators 131 exchange parameters (but not sample data) amongst themselves without the use of a centralized server.

The local data for each collaborator 131 is validated/curated. Data curation promotes enhanced federated learning training stability and generalizability without violating privacy preservation. The validation/curation may be performed remotely or locally. When performed remotely, an anonymized portion of the sample data is transmitted to a validation server that determines if the data sample meets data selection conditions for the model. Similarly, when performed locally, an anonymized portion of the sample data is input into a machine trained classifier that determines if the data sample meets data selection conditions for the model.

Figure 2:
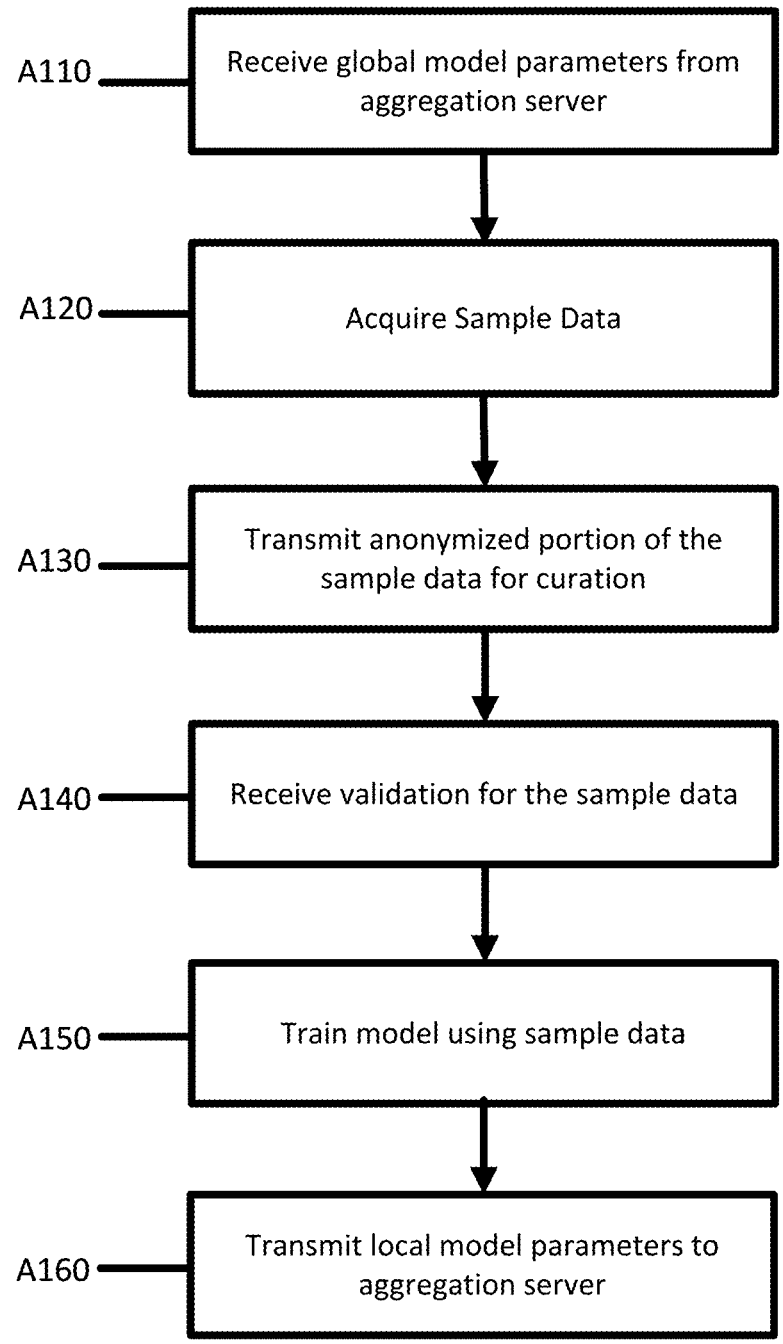
FIG. 2 depicts an example method for adaptive aggregation of model parameters according to an embodiment.

FIG. 2 depicts a method for data curation for a plurality of collaborators 131 in a federated learning system that trains a model over multiple rounds of training. The workflow describes one potential round of multiple rounds of training that are to be performed. There may be tens, hundreds, thousands, or more rounds performed until the model is trained. For each round, the collaborators 131 or remote devices train a local model with local data. Local model parameters are then sent to an aggregation server 121 that is configured to aggregate the parameters from multiple collaborators 131 into a single central model. The parameters for the single central model are transmitted from the aggregation server 121 back to the collaborators 131 for a subsequent round of training. As presented in the following sections, the acts may be performed using any combination of the components indicated in FIG. 1, 3, or 4. The following acts may be performed by the collaborators 131, an aggregation server 121, a cloud-based server, or a combination thereof. Additional, different, or fewer acts may be provided. The acts are performed in the order shown or other orders. The data curation may take place at any point during the round or rounds of federated learning. The acts may also be repeated. Certain acts may be skipped or adjusted depending on the federated learning scheme. For example, in a peer-to-peer federated learning system, there is no aggregation server 121. Instead, the collaborators 131 share parameters amongst themselves without a centralized controller.

Figure 3:
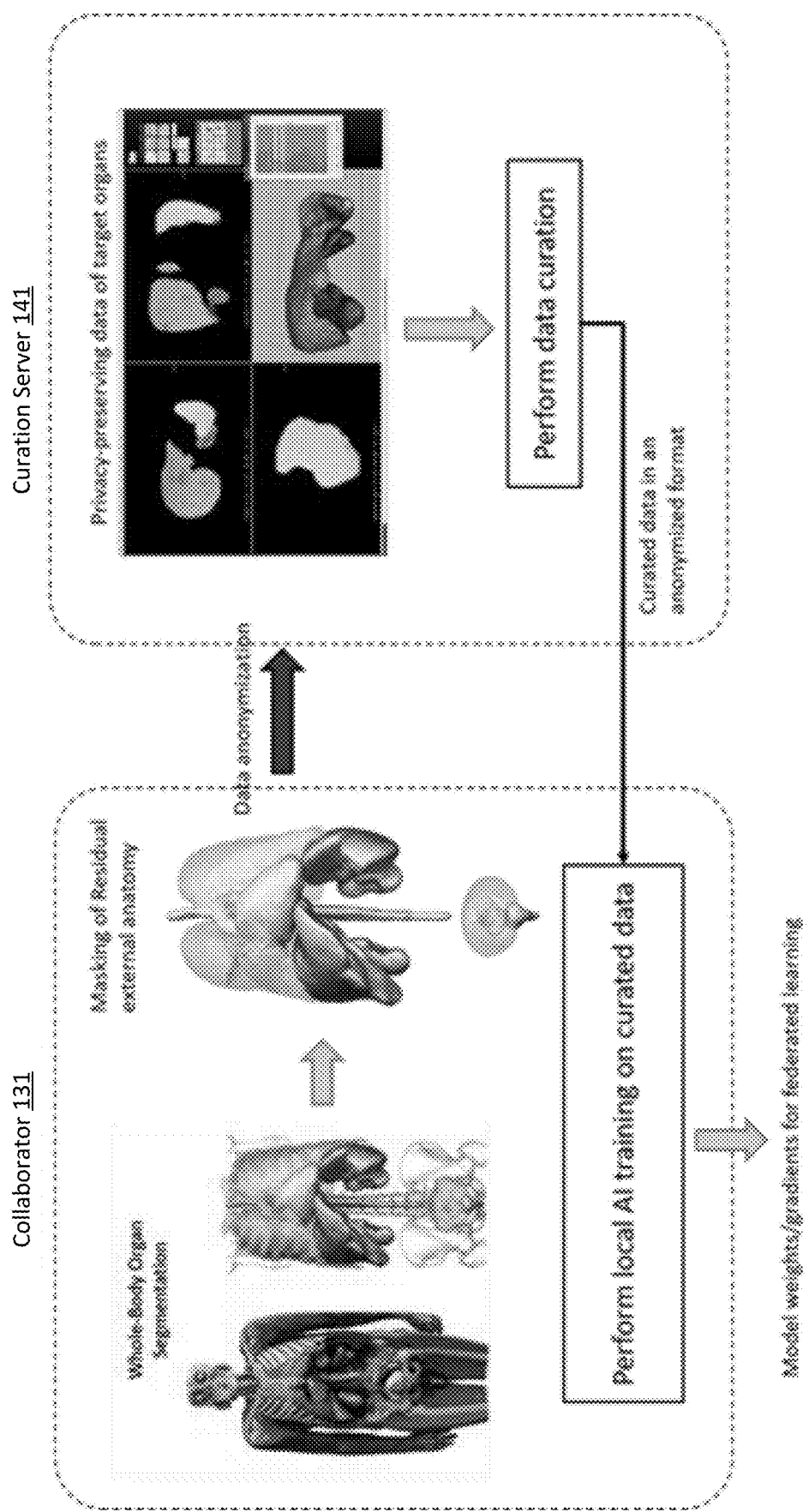
FIG. 3 depicts an example workflow for adaptive aggregation of model parameters according to an embodiment.

FIG. 3 depicts an example of the curation process. In FIG. 3, a collaborator 131 segments a whole body. The collaborator 131 masks residual anatomy which anonymizes the patient data. The sample data is transmitted to a curation server 141 that is configured to perform data curation of the masked data. Curated data or validation is sent back to the collaborator 131 that performs local training in combination with other collaborators 131.

At act A110, a collaborator 131 of the plurality of collaborators 131 receives global model parameters from a parameter aggregation server 121. The collaborators 131 may be remotely located from the aggregation server 121. In an embodiment, the collaborators 131 are hospital sites. The collaborators 131 are configured to train a model using locally acquired data that, for privacy or security reasons, does not leave the site of the respective collaborator 131. Each collaborator 131 acquires data, trains a model for one or more epochs, and then transmits model parameters to the aggregation server 121 over a network. The aggregation server 121 may include one or more machines or servers. A hierarchy of aggregation servers may be used to receive the model parameters which may be further aggregated by an additional server. The aggregation servers 121 may be configured to operate in the cloud or on multiple different machines. In an embodiment, the aggregation server 121 and collaborators 131 are remotely located. Alternatively, the aggregation server 121 and collaborators 131 may be co-located. The aggregation server 121 and collaborators 131 communicate using the network that may include wired networks, wireless networks, or combinations thereof. The wireless network may be a cellular telephone network, LTE (Long-Term Evolution), 4G LTE, a wireless local area network, such as an 802.11, 802.16, 802.20, WiMax (Worldwide Interoperability for Microwave Access) network, DSRC (otherwise known as WAVE, ITS-G5, or 802.11p and future generations thereof), a 5G wireless network, or wireless short-range network. Further, the network 127 may be a public network, such as the Internet, a private network, such as an intranet, or combinations thereof, and may utilize a variety of networking protocols now available or later developed including, but not limited to transmission control protocol/internet protocol (TCP/IP) based networking protocols.

The model may be any model that is trained using a machine learning process. Examples for medical applications include finding clinically similar patients, predicting hospitalizations due to cardiac events, mortality and ICU stay time. Models may also include applications in the field of medical imaging such as for whole-brain segmentation as well as brain tumor segmentation, for example. In an embodiment, the model may be used to identify disease-related biomarkers in the context of COVID-19.

The model parameters may be represented by one or more parameter vectors. A parameter vector may be a collection (e.g., set) of parameters from the model or a representation of the set of parameters. The parameter vector may be a randomly chosen components of a parameter vector. Models may include thousands or millions of parameters. Compressing the set of parameters into a parameter vector may be more efficient for bandwidth and timing than transmitting and recalculating each parameter of the set of parameters. A parameter vector may also be further compressed. In an embodiment, an incoming parameter vector may also be compressed into a sparse subspace vector.

In an embodiment, the model is trained using a supervised learning process. A supervised learning process may be used to predict numerical values (regression) and for classification purposes (predicting the appropriate class). A supervised learning processing may include processing images, audio files, videos, numerical data, and text among other types of data. Classification examples include segmentation, object recognition, face recognition, credit risk assessment, voice recognition, and customer churn, among others. Regression examples include determining continuous numerical values on the basis of multiple (sometimes hundreds or thousands) input variables.

The model may include machine learned processes such as support vector machine (SVM), boosted and bagged decision trees, k-nearest neighbor, Naive Bayes, discriminant analysis, logistic regression, and neural networks. In an example, a two-stage convolutional neural network is used that includes max pooling layers. The two-stage convolutional neural network (CNN) uses rectified linear units for the non-linearity and a fully connected layer at the end for image classification. In an embodiment, the model may be trained using an adversarial training process, e.g., the model may include a generative adversarial network (GAN). For an adversarial training approach, a generative network and a discriminative network are provided for training by the devices. The generative network is trained to identify the features of data in one domain A and transform the data from domain A into data that is indistinguishable from data in domain B. In the training process, the discriminative network plays the role of a judge to score how likely the transformed data from domain A is similar to the data of domain B, e.g., if the data is a forgery or real data from domain B. In an embodiment, the model is applicable to a medical diagnosis, for example, a classification network configured to identify or diagnosis a disease or issue when input an image or volume.

At act A120, the collaborator 131 acquires sample data. The training data for each of the collaborators 131 is not independently and identically distributed (non-I.I.D.). The distribution of data for two different collaborators 131 is different and unbalanced (for example, the collaborators 131 have different orders of magnitudes of acquired data). In an example, for image data, one device may have several gigabytes of medical imaging data that relates to images taken for multiple procedures for multiple patients while another has only a single set of image data. Both sets of data may be useful to train a segmentation model though the collaborator 131 with more data may provide more useful parameters. The quality of data may also differ between devices. Certain devices may include higher quality sensors or may include more storage for data allowing higher quality data to be captured.

The collaborators 131 are configured to train or configure a local model using the training data. In an embodiment, the training data is labeled. Labeled data is used for supervised learning. The model is trained by imputing known inputs and known outputs. Weights or parameters are adjusted until the model accurately matching the known inputs and output. In an example, to train a machine learned model to identify certain artifacts using acquired image data, images of the artifacts—with a variety of configurations—are required as input variables. The labels, e.g., the correct designations, for such data may be assigned manually or automatically. The correct set of input variables and the correct classifications constitute the training data set. Labels may be provided by, for example, requesting additional input from a user (requesting a manual annotation), derived from additional data (parsing textual descriptions), or by incorporating additional data from other sources. Other methods for labeling data may be used, for example, a cloud-based service may give accurate, albeit incomplete, labels that be downloaded from the cloud to the device. The sample data, may, for example, be medical imaging data including images (2D) or volumes (3D) of imaging data of a patient.

At act A130, the collaborator 131 transmits an anonymized portion of the sample data to a curation server 141 configured to identify data samples that don't meet data selection conditions. As described above, the data sample may be, for example, imaging data of a patient. In an embodiment, the collaborator 131 utilizes a full-body organ segmentation to extract an anatomical area of interest (e.g., a brain, a lung) that needs to be curated and masks out the remaining part of the image such that identifying the individual patient is impossible. The mask data includes the same resolution, orientation, and image quality (SNR, sharpness/contrast) in the anatomical area of interest as the original volume data so that a remote examiner can apply the same data curation criteria.

In an embodiment, the anonymized portion is an anatomical area of a volume/imaging data that is not relevant to the diagnosis. The anonymized portion, however, may provide an indication of the quality of the entirety of the full body segmentation. The anonymized portion may thus be used as a proxy for the relevant portion while still maintaining the privacy and security for the diagnosis of the patient. In an example, the portion may include or be a non-relevant organ, for example a lung when the diagnosis is concerning a brain of the patient. As detailed below, if the lung segmentation is low quality, the brain segmentation may also be as well and thus the data sample may be set aside for further review.

In a further embodiment, the anonymized portion of the sample data is inputted into a machine trained model that is configured to output a classification or indication of quality. The machine trained curation classification model may be centrally trained and then implemented at each site. The collaborators 131 submit their data samples locally to the machine trained curation classification model. Alternatively, the machine trained curation classification model may be trained using a federated learning method. In such a scenario, the machine trained curation classification model is first trained to curate data which is then used to train the main model.

At act A140, the collaborator 131 receives validation for the sample data from the curation server 141. The curation server 141 may perform one or more validation tasks on the sample data to determine if the sample data is sufficient to be used to train the model. Since the sample data is only a portion of the data, the patient remains anonymous. In an embodiment, the sample data may be reviewed by remote examiners. The remote examiners may focus on visually checking the region of interest. The remote examiners are not able to see any other identifiable subject information such as face, body shape etc. as the pixels or voxels outside the segmentation mask are blanked out or not included. The masked data includes the same resolution, orientation, and image quality (SNR, sharpness/contrast) in the anatomical area of interest as the original volume data, so the remote examiner is able to apply the same data curation criteria. The examination results are sent back to the collaborators 131 so that inappropriate data samples can be excluded during federated learning rounds. In an embodiment, if a data sample does not meet the data curation criteria, the data sample may be flagged for local review. The local review process may be performed by a clinician or operator and may include identifying issues with the data sample and correct or fixing the issues and resubmitting the data samples to the curation server 141.

In an embodiment, the curation server 141 may perform an outlier detection approach for validation of the sample data. The outlier detection approach mainly treats low-quality data as outliers by exploring the statistical property, distance-based features, clustering-based, and density-based ones. An example of an outlier detection approach includes the AVF (Attribute Value Frequency) algorithm. In outlier detection-based data cleaning approaches, data sample are identified as outliers if they are located far away from the majority of all the data. For an outlier detection-based approach, only certain metrics or properties of the sample data may be provided to the curation server 141, for example that describe the statistical properties of the sample data or region of interest.

Another approach may include using a machine learning-based classifier. In an embodiment, AI classification networks may be implemented for each data curation criterion that can automatically identify data samples that don't meet data selection conditions. The classification networks maybe trained on a centralized dataset or a local dataset, and in an embodiment, may be subsequently deployed to collaborators 131. A subset of data samples that have low confidence classification scores identified by the AI method may be sent to examiners for manual visual inspection using the method above.

At act A150, the collaborator 131 trains the model using the validated sample data. The sample data that is not validated may be set aside or manually reviewed on site.

Alternatively, the poor-quality sample data may be used, but an indication that the quality is low may be transmitted to the aggregation server that may discount the parameters from the particular collaborator 131. In an embodiment, the model is trained using a gradient descent technique or a stochastic gradient descent technique. Both techniques attempt to minimize an error function defined for the model. For training (minimizing the error function), a collaborator 131 first connects to the parameter server. The collaborator 131 may start with randomly initialized model parameters or may request initial model parameters from the parameter server. The starting parameters may also be derived from another, pretrained model rather than being randomly initialized. The initial parameters may be assigned to all subsequent collaborators 131. Alternatively, updated central parameters may be assigned if the training process has already begun. In an example, collaborators 131 may initially communicate with the parameter server at different times. A first collaborator 131 may communicate with the aggregation server 121 and be assigned randomly initialized model parameters. Similarly, a second collaborator 131 may communicate shortly thereafter with the aggregation server 121 and be assigned randomly initialized model parameters. At some point, the collaborators 131 begin transmitting model parameters back to the aggregation server 121. As detailed below, the aggregation server 121 updates the central model parameters and transmits the updated model parameters back to the collaborators 131. Any collaborator 131 that first communicates with the parameter server after this time may be assigned the central parameters and not the randomly initialized model parameters. In this way, new collaborators 131 may be added to the system at any point during the training process without disrupting the training process. Handing out the latest parameters to newly joined collaborators 131 may result in faster learning at early stages.

The gradient descent technique attempts to minimize an error function for the model. Each collaborator 131 trains a local model using local training data. Training the model involves adjusting internal weights or parameters of the local model until the local model is able to accurately predict the correct outcome given a newly input data point. The result of the training process is a model that includes one or more local parameters that minimize the errors of the function given the local training data. The one or more local parameters may be represented as a parameter vector. As the local training data is limited the trained model may not be very accurate when predicting the result of an unidentified input data point. The trained model, however, may be trained to be more accurate given starting parameters that cover a wider swath of data. Better starting parameters may be acquired from the aggregation server 121.

At act A160, the collaborator 131 transmits local model parameters for the model to the parameter aggregation server. The aggregated model parameters are used by the plurality of collaborators 131 for a subsequent round of training. The subsequent round is similar to the described round of A110-A160. The difference for each iteration is a different starting point for one or more of the parameters in the model. The central parameter vector that is received may be different than the local parameter vector provided in A110. The process repeats for a number of iterations until the parameters converge or a predetermined number of iterations are reached. This process may be repeated hundreds or thousands of times. In an example, several hundred (e.g., 100 to 500) or thousand (e.g., 3,000 to 5,000) iterations may be performed. Depending on the complexity of the model and the type and quantity of devices and data, more or fewer iterations may be performed. If new data is added to the training data, the device may retrain the model and request a new central parameter (and the process may be fully or partially repeated). The result of the training process is a model that may be able to, for example, accurately predict a classification given an unlabeled input. The model is used on new data to generate, for example, a prediction or classification. In an example, for an image classification model, the collaborator 131 identifies an object or feature in newly acquired (unseen) imaging data using the trained machine learned model.

In an embodiment, a machine trained model is deployed to each of the collaborators 131 to curate the data. The machine trained model may be trained, stored, and updated at a curation server. After being trained, the machine trained model may be transmitted to the collaborators 131 which then submit their data samples locally to the model in order to be curated.

In an embodiment, the data curation may be applied to training a model for use in medical applications. In medical applications, deep learning has the potential to create significant tools for the screening and diagnosis of medical issues, for example recently COVID-19. Nevertheless, access to large, diverse healthcare datasets remains a challenge due to regulatory concerns over sharing protected healthcare information. One issue representing a stark deterrent from multi-institutional/multi-national AI trials is the rigorous regulation of patient data and the requirements for its protection. Both the United States Health Insurance Portability and Accountability Act (HIPAA) and the European General Data Protection Regulation (GDPR) mandate strict rules regarding the storage and exchange of personally identifiable data and data concerning health, requiring authentication, authorization, accountability and—with GDPR—AI interpretability, sparking considerations on data handling, ownership, and AI governance. Ethical, moral, and scientific guidelines) also prescribe respect towards privacy—that is, the ability to retain full control and secrecy about one's personal information. The lack of standardized, electronic patient records is another reason. Electronic patient data management is expensive, and hospitals in underprivileged regions might be unable to afford participation in studies requiring it, potentially perpetuating the aforementioned issues of bias and fairness. The decentralized nature of the data complicates data curation to ascertain the integrity and quality of the results. Using a data curation scheme as described above can alleviate some of the issues and allow the federated learning process to generate accurate and useful models. An example of the type of model that can used with federated learning and makes use of the data curation described above is provided below.

In an embodiment, adaptive aggregation is used to overcome previous issues with the application of FL to COVID-19 diagnosis. One trained model uses a chest computed tomography (CT) scan that is more sensitive for COVID-19 diagnosis and is currently widely applied for early screening of the disease. A segmentation network is used that can automatically quantify abnormal computed tomography (CT) patterns commonly present in COVID-19 patients. A second trained model uses a classification network that can automatically detect COVID-19 pathology and differentiate from other pneumonias, interstitial lung diseases (ILD) and normal subjects in chest CTs. In an embodiment, the sample data, for example, a full body (or partial) segmentation is masked out to exclude everything but the lungs. The masked-out volume is validated either remotely or by a machine trained classification network. Once validated, the volume may be used by a collaborator 131 to train a network to detect and/or diagnosis COVID-19.

In an embodiment, the segmentation network includes a U-Net resembling architecture with 3D convolution blocks containing either 1 3 3 or 3 3 3 CNN kernels to deal with anisotropic resolutions. The 3D input tensor is fed into a 3D 1 3 3 convolutional layer followed by batch normalization and leaky ReLU. The feature maps were then propagated to 5 DenseNet blocks. For the first two DenseNet blocks, the features are downsampled by a 1 2 2 convolution with a stride of 1 2 2. The anisotropic downsampling kernels are configured to preserve the inter-slice resolution of input image volumes. The last three DenseNet blocks include isotropic downsampling kernels with the stride of 2 2 2. The input to each decoder block is obtained by concatenating the encoder output features with the same resolution and the feature maps upsampled from the previous decoder. The upsampling kernels are built with transpose convolutional kernels with the sizes and strides same to the corresponding DenseNet blocks. The final network output is derived by projecting the feature maps to 2 output channels and activated by softmax operation.

In an embodiment, the classification network is configured for COVID-19 pathology differentiation on chest CT data, that extracted both 2D axial features and 3D global features. The network includes a ResNet50 as the backbone axial feature extractor, that takes a series of CT in-plane slices as input and generated feature maps for the corresponding slices. The extracted features from all slices are then combined by a max-pooling operation. The global feature is fed to a fully connected layer that produces a COVID-19 prediction score per case by softmax operation.

For each model, during the federated learning, data curation is used to deal with the non-I.I.D. data from each hospital site. Data curation allows the model to be trained efficiently without being polluted by low quality training rounds due to low quality or insufficient data samples.

Figure 4:
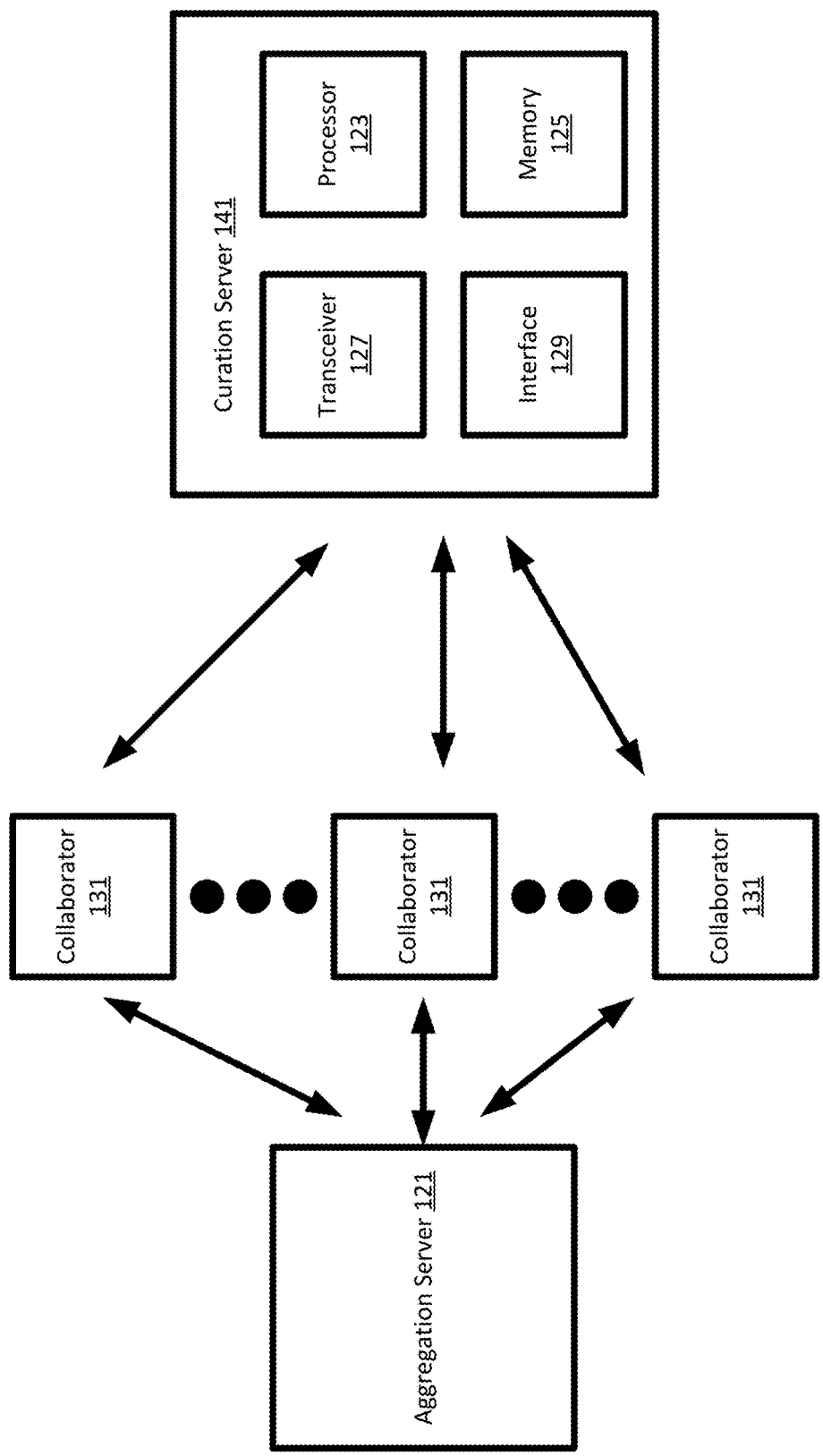
FIG. 4 depicts an example aggregation server according to an embodiment.

FIG. 4 depicts an example of a curation server 141. The curation server 141 includes at least a memory 125, a processor 123, an interface 129, and a transceiver 127. The curation server 141 may communicate with one or more collaborators 131 or sites using the transceiver 127 to receive sample data and transmit validation data. The one or more collaborators 131 may include hospital sites or centers otherwise equipped to acquire or store medical data for patients. For example, the one or more collaborators 131 may include medical imaging devices and/or PACS systems configured to acquire or store medical imaging data for use in training a model and generating model parameters.

The memory 125 may be a non-transitory computer readable storage medium storing data representing instructions executable by the processor 123 for time-varying readmission risk prediction. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system. The memory 125 may store a model or machine learnt network.

The processor 123 is a general processor, central processing unit, control processor, graphics processing unit, digital signal processor, three-dimensional rendering processor, image processor, application specific integrated circuit, field programmable gate array, digital circuit, analog circuit, combinations thereof, or other now known or later developed device for processing medical imaging data. The processor 123 is a single device or multiple devices operating in serial, parallel, or separately. The processor 123 may be a main processor of a computer, such as a laptop or desktop computer, or may be a processor for handling some tasks in a larger system, such as in a server. The processor 123 is configured by instructions, design, hardware, and/or software to perform the acts discussed herein.

The processor 123 may be configured to receive sample data from one or more collaborators 131, examine the data, and return a determination of whether the sample data meets data curation criteria set by, for example, an administrator of the model or federated learning process. In an embodiment, the remote examination focuses on visually checking a region of interest for the data sample. The data reviewed by the processor may only include a portion of the data sample stored at the collaborator 131. For example, the collaborator 131 may mask out part of the image or volume such that identifying an individual patient is impossible. The examination by the processor 123 may thus not be able to see any identifiable subject information such as face, body shape etc. of the patient because pixels or voxels outside the mask are blanked out. The mask data includes the same resolution, orientation, and image quality (SNR, sharpness/contrast) in the anatomical area of interest as the original volume data so the remote examiner could apply the same data curation criteria. The examination results are sent back to the collaborators 131 so that inappropriate data samples can be excluded during federated learning rounds.

The processor 123 may be configured to implement a machine learned classification model that is configured to identify data samples that meet data curation criteria. The machine learned classification model may be stored in the memory 125. The machine learned classification model may be trained using a set of training data that includes data sample that do and do not meet the data curation criteria. The processor 123 may implement multiple models for different criteria. The machine learned classification model(s) may be trained using supervised or unsupervised learning. The machine learned classification model(s) may include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes. Unsupervised learning may also be used based on the distribution of the samples, using methods such as k-nearest neighbor.

Different neural network configurations and workflows may be used for or in the machine learned classification model such as a convolution neural network (CNN), deep belief nets (DBN), or other deep networks. CNN learns feed-forward mapping functions while DBN learns a generative model of data. In addition, CNN uses shared weights for all local regions while DBN is a fully connected network (e.g., including different weights for all regions of a feature map. The training of CNN is entirely discriminative through backpropagation. DBN, on the other hand, employs the layer-wise unsupervised training (e.g., pre-training) followed by the discriminative refinement with backpropagation if necessary. In an embodiment, the arrangement of the trained network is a fully convolutional network (FCN). Other network arrangements may be used, for example, a 3D Very Deep Convolutional Networks (3D-VGGNet). VGG-Net stacks many layer blocks containing narrow convolutional layers followed by max pooling layers. A 3D Deep Residual Networks (3D-ResNet) architecture may be used. A Resnet uses residual blocks and skip connections to learn residual mapping.

The training data for the machine learned classification model includes ground truth data or gold standard data acquired at each collaborator 131 or site. Ground truth data and gold standard data is data that includes correct or reasonably accurate labels that are verified manually or by some other accurate method. The training data may be acquired at any point prior to inputting the training data into the model. Each machine learned classification model may input the training data (e.g., patient data) and output a prediction or classification, for example that indicates that the data is acceptable based on one or more data criteria (such as quality, resolution, etc.). The prediction is compared to the annotations from the training data. A loss function may be used to identify the errors from the comparison. The loss function serves as a measurement of how far the current set of predictions are from the corresponding true values. Some examples of loss functions that may be used include Mean-Squared-Error, Root-Mean-Squared-Error, and Cross-entropy loss. Mean Squared Error loss, or MSE for short, is calculated as the average of the squared differences between the predicted and actual values. Root-Mean Squared Error is similarly calculated as the average of the root squared differences between the predicted and actual values. For cross-entropy loss each predicted probability is compared to the actual class output value (0 or 1) and a score is calculated that penalizes the probability based on the distance from the expected value. The penalty may be logarithmic, offering a small score for small differences (0.1 or 0.2) and enormous score for a large difference (0.9 or 1.0). During training and over repeated iterations, the network attempts to minimize the loss function as the result of a lower error between the actual and the predicted values means the network has done a good job in learning. Different optimization algorithms may be used to minimize the loss function, such as, for example, gradient descent, Stochastic gradient descent, Batch gradient descent, Mini-Batch gradient descent, among others. The process of inputting, outputting, comparing, and adjusting is repeated for a predetermined number of iterations with the goal of minimizing the loss function. Once adjusted and trained, the model is configured to be applied. In an embodiment, the trained model may be deployed to each of the collaborators 131. The collaborators 131 may apply the model to locally curate data with a standardized curation criteria.

The curation server 141 may also include an interface device having a display, e.g., a CRT (cathode ray tube) or LCD (liquid crystal display) monitor, for displaying information to a user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input. The interface may include one or more buttons, keypad, keyboard, mouse, stylus pen, trackball, rocker switch, touch pad, voice recognition circuit, or other device or component for inputting data to the curation server 141 while reviewing the sample data.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:
1. A method for training a model using federated learning by a plurality of collaborator computing devices, the method comprising:
receiving, by a collaborator computing device of the plurality of collaborator computing devices, global model parameters from a parameter aggregation server;
acquiring, by the collaborator computing device, sample data;
transmitting, by the collaborator computing device, an anonymized portion of the sample data to a curation server configured to validate data samples that meet one or more data selection conditions;
receiving, by the collaborator computing device from the curation server, validation for the sample data;
training, by the collaborator computing device, the model using the validated sample data; and
transmitting, by the collaborator computing device, local model parameters for the model to the parameter aggregation server.
2. The method of claim 1, wherein the anonymized portion of the sample data comprises a masked portion of the sample data.
3. The method of claim 2, wherein the mask portion includes a same resolution, an orientation, and a signal to noise ratio in an anatomical area of interest as the sample data.

4. The method of claim 2, wherein one or more entities at the curation server are unable to identify subject information of the sample data based on the masked portion.

5. The method of claim 1, wherein the validation comprises a classification confidence score for the sample data, wherein the collaborator computing device is configured to only use sample data that exceeds a threshold classification confidence score.

6. The method of claim 1, wherein the curation server comprises a machine trained classification network configured to classify the anonymized portion of the sample data as meeting or not meeting the one or more data selection conditions.

7. The method of claim 1, wherein the model comprises an image classification model for performing a medical diagnosis, wherein the sample data comprises medical imaging data for a patient.

8. The method of claim 1, wherein identifying data samples that do or do not meet the one or more data selection conditions comprises identifying outlier data samples.

9. The method of claim 1, wherein data samples that do not don't meet the one or more data selection conditions are flagged for manual review by a clinician.

10. A method for training a model using federated learning by a plurality of collaborator computing devices, the method comprising:
 receiving, by a collaborator computing device of the plurality of collaborator computing devices, global model parameters from a parameter aggregation server;
 acquiring, by the collaborator computing device, sample data;
 transmitting, by the collaborator computing device, an anonymized portion of the sample data to a remote site, the remote site including a machine trained network;
 identifying, at the remote site by the machine trained network, that the sample data is valid by meeting one or more data selection conditions;
 receiving, by the collaborator computing device from the machine trained network, validation for the sample data;
 training, by the collaborator computing device, a model using the validated sample data; and
 transmitting, by the collaborator computing device, local model parameters for the model to the parameter aggregation server.

11. The method of claim 10, wherein the anonymized portion of the sample data comprises a masked portion of the sample data.

12. The method of claim 11, wherein the mask portion includes a same resolution, an orientation, and an image quality in an anatomical area of interest as the sample data.

13. The method of claim 10, wherein the validation comprises a classification confidence score for the sample data, wherein the collaborator computing device is configured to only use sample data that exceeds a threshold classification confidence score.

14. The method of claim 10, wherein the machine trained model comprises an image classification model for performing a medical diagnosis, wherein the sample data comprises medical imaging data for a patient.

15. The method of claim 10, wherein identifying data samples that are valid comprises identifying and excluding outlier data samples.

16. The method of claim 10, wherein data samples that do not meet the one or more data selection conditions are flagged for manual review by a clinician.

17. A system for federated learning, the system comprising:
 a plurality of collaborator computing devices, each collaborator computing device of the plurality of collaborator computing devices configured to acquire sample data, anonymize the sample data, and transmit the anonymized sample data to a curation server for validation, each collaborator computing device further configured to train a local machine learned model using validated sample data, update local model weights for the local machine learned model, and send the updated local model weights to an aggregation server;
 a curation server configured to receive the anonymized sample data and validate sample data that meets one or more data selection conditions; and
 the aggregation server configured to receive the updated model weights from the plurality of collaborator computing devices, calculate aggregated model weights, and transmit the aggregated model weights to the plurality of collaborator computing devices to update the local machine learned model.

18. The system of claim 17, wherein each collaborator computing device is configured to anonymize the sample data by masking out region that do not include a region of interest while maintaining a same resolution, an orientation, and a signal to noise ratio as the sample data.

19. The system of claim 17, wherein the curation server includes a machine trained model configured to identify sample data that meets the one or more data selection conditions.

20. The system of claim 17, wherein the local machine learned model comprises an image classification model for performing a medical diagnosis, wherein the sample data comprises medical imaging data for a patient.

* * * * *